United States Patent [19]

Knorre et al.

[11] 4,416,786

[45] Nov. 22, 1983

[54] PROCESS FOR THE TREATMENT OF CONTINUOUS WASTE WATER STREAMS HAVING CHANGING CONTENTS OF DIFFERENT OXIDIZABLE MATERIALS WITH HYDROGEN PEROXIDE

[75] Inventors: Helmut Knorre, Seligenstadt; Joachim Fischer, Rodenbach; Klaus Stützel, Frankfurt, all of Fed. Rep. of Germany

[73] Assignee: Degussa, Frankfurt, Fed. Rep. of Germany

[21] Appl. No.: 392,464

[22] Filed: Jun. 28, 1982

[30] Foreign Application Priority Data

Jun. 29, 1981 [DE]  Fed. Rep. of Germany ....... 3125452

[51] Int. Cl.³ ............................................... C02F 1/72
[52] U.S. Cl. .................................... 210/746; 210/759; 210/908; 210/904; 210/916
[58] Field of Search ................ 210/739, 743, 758–760, 210/790, 904, 908, 916, 746

[56] References Cited

U.S. PATENT DOCUMENTS

| | | | |
|---|---|---|---|
| 3,843,516 | 10/1974 | Yamada et al. | 210/904 X |
| 3,970,554 | 7/1976 | Fischer . | |
| 4,104,162 | 8/1978 | Tunkermann et al. | 210/759 |
| 4,160,656 | 7/1979 | Tunkermann | 210/759 X |
| 4,268,397 | 5/1981 | Horie et al. | 210/746 |
| 4,280,914 | 7/1981 | Knorre et al. | 210/759 X |
| 4,340,490 | 7/1982 | Tunkermann | 210/908 X |

FOREIGN PATENT DOCUMENTS 2352856  4/1975  Fed. Rep. of Germany .

*Primary Examiner*—Thomas G. Wyse
*Attorney, Agent, or Firm*—Cushman, Darby & Cushman

[57] ABSTRACT

There is provided a continuous process for the lowering of the content of toxic materials in waste waters which also contain other oxidizable materials by quickly and continuously ascertaining the requirement of hydrogen peroxide, namely by potentiometric determination of the oxidizing agent requirement in a branched-off sidestream using a strong oxidizing agent, such as peroxymonosulfate, peroxydisulfate, permanganate, hypochlorite or ozone, which acts more quickly than hydrogen peroxide under comparable conditions.

20 Claims, 2 Drawing Figures

PROCESS FOR THE TREATMENT OF CONTINUOUS WASTE WATER STREAMS HAVING CHANGING CONTENTS OF DIFFERENT OXIDIZABLE MATERIALS WITH HYDROGEN PEROXIDE

BACKGROUND OF THE INVENTION

The use of hydrogen peroxide as an agent for the oxidative treatment of waste water takes on increasing significance under today's aspects of environmental protection, since hydrogen peroxide itself does not cause additional salting of the waste water but splits into water and oxygen. However, an essential condition is that the necessary amount of hydrogen peroxide can be determined automatically and controlled.

This requirement is especially true for the treatment of continuous waste water streams which contain variable amounts of different oxidizable toxic materials and only permit a relatively short time for treatment. In such cases the success of waste water treatment with hydrogen peroxide depends highly on how quickly and reliably the total requirements of oxidizing agent can be determined in the incoming waste water stream in the treatment plant. As total oxidizing agent demand (requirement) we understand that amount of active oxygen or $H_2O_2$ which is needed in order to be able to convert the oxidizable material in the waste water under the chosen reaction conditions into the appropriate oxidation products in each case.

Little information can be found in the technical literature as to how the total oxidizing agent requirement of a waste water can be determined automatically. The reason for this is that most of the materials occurring in waste water only contribute in small and very variable manner to the formation of a definite redox potential, that e.g. can be measured with a platinum/reference electrode pair. Therefore the oxidative waste water treatment process is operated in such a way that, while following the redox potential of the waste water, oxidizing agent is added successively until due to the presence of an excess a constant end point is established. However, in most cases this process is usable only for a batchwise treatment of waste water, since the oxidation of the various materials with $H_2O_2$ requires variable reaction times and therefore a constant end potential is not established immediately, even in the presence of excess $H_2O_2$, but only when the oxidation reactions are completed.

Thus, e.g., there is described in German Pat. No. 2,352,856 and related Fischer U.S. Pat. No. 3,970,554 a process for the detoxification of cyanide-containing waste water with $H_2O_2$ that permits the monitoring and control of the detoxification process and the addition of the $H_2O_2$ by measuring the redox potential with a silver electrode and any desired reference electrode, preferably a thalamide electrode. (The entire disclosure of the Fischer U.S. patent is hereby incorporated by reference and relied upon). However, this process is only employable in most cases for a batchwise treatment of waste water since the measurement of the redox potential shows the free cyanide content in the waste water, but permits no conclusions regarding the total oxidizing agent requirement if, besides free cyanides, other consumers of hydrogen peroxide are also contained in the waste water.

The single addition of an amount of oxidizing agent corresponding to the indication of free cyanide content at the beginning of the waste water treatment would accordingly lead to insufficient detoxification results, because the other consumers of $H_2O_2$ use up a portion of the hydrogen peroxide which is needed for the cyanide oxidation. Only through multiple subsequent dosing of oxidizing agent at fixed time intervals can in these cases bring about both the desired breakdown of cyanide as well as of other oxidizable materials present. Such a stepwise approach to the goal of the process, as necessary because of the reaction time needed for the oxidation of the cyanide, does not usually permit the continuous treatment of large waste water streams because the treatment plant must be constructed so large in order to guarantee sufficient treatment time.

In Belgian Pat. No. 883,046 there is given a process for the measurement of the concentration of a specific dissolved component with redox- or ion-sensitive electrodes for the purpose of monitoring or regulating chemical processes, among others in the treatment of waste water. This process is characterized by the determination of the maximum attainable potential value by addition of excess reagent to a side stream of the system and evaluating the deviation of the starting potential as a measure of the reactive material content. For example, in this way the free cyanide content can be ascertained quickly and reliably in a continuous waste water stream and the amount of hydrogen peroxide shown to be required for the oxidation can be added. However, the process described according to Belgian Pat. No. 883,046 fails to work if there are present in waste water different oxidizable toxic materials in varying concentrations together which contribute different amounts to the formation of the redox potential. Thus, e.g., in the measurement of the cyanide potential with a silver electrode and a thalamide reference electrode under the conditions of the process described in German Pat. No. 2,352,856 (and related Fischer U.S. patent) approximately the same redox potential of about 350 mV is produced by 1 mg $S^{2-}$ 1 as by 50 mg Cn/l. Other oxidizable materials, such as sulfite, on the other hand are practically not detected at all by this redox system.

Therefore the invention is based on the problem of developing automatic system which makes possible quick and reliable determination of the oxidizing agent requirement which is needed for decreasing the toxic material concentration of a waste water under a desired limit in a continuous oxidative treatment of the waste water under fixed pH and temperature conditions.

SUMMARY OF THE INVENTION

It has now been found that this problem of the treatment of continuous waste water streams with varying contents of different oxidizable materials, especially cyanides, sulfides, sulfites, thiosulfates, thiocyanates and/or organic materials, with hydrogen peroxide for the purpose of the detoxification and reduction of the chemical and biological oxygen demand can be solved if the dosing of the $H_2O_2$ to the continuous waste water stream (main stream) is controlled by ascertaining the oxidizing agent demand in a small, continuously branched-off side-stream (measuring stream) parallel thereto by:

(a) adjusting the pH of the waste water in the side-stream by dosing of alkali or acid to a definite value between pH 3 and 12;

(b) continuously measuring the redox potential in the side-stream in the known manner with a platinum, silver, gold, or ion-selective electrode and any suitable reference electrode and dosing an aqueous solution of a strong oxidizing agent acting more quickly than $H_2O_2$ under comparable conditions, such oxidizing agent preferably being a peroxymonosulfate, peroxydisulfate, hypochlorite, permanganate or ozone, until the desired redox value is reached corresponding to the sought breakdown of the toxic material, and then always, when the strong oxidizing agent is dosed into the side-stream (measuring stream) simultaneously adding proportional amounts of $H_2O_2$ and other chemicals if necessary, e.g., for pH regulation, into the main-stream.

DETAILED DESCRIPTION

Figure 1:
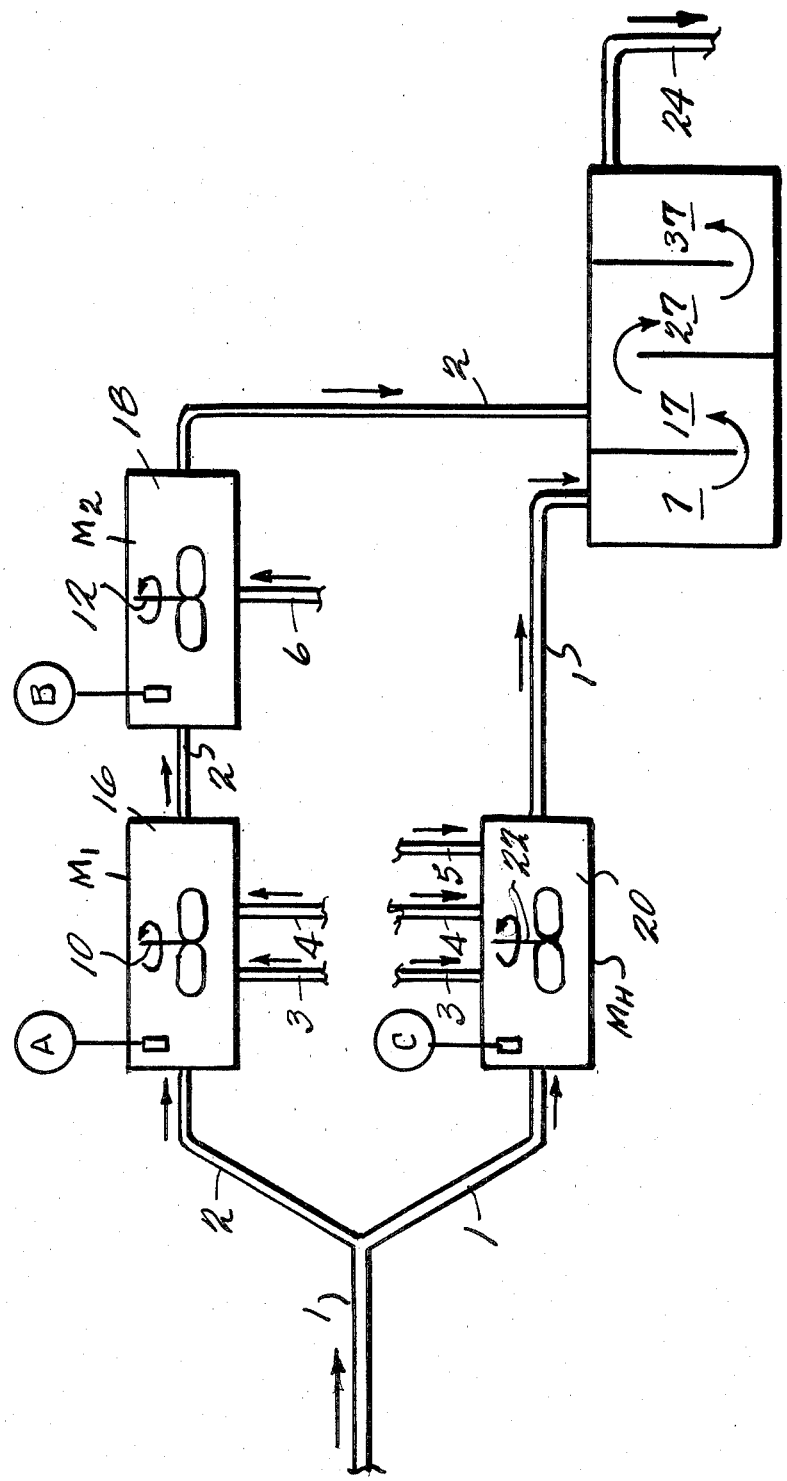
FIG. 1 is a schematic flow diagram of one form of the process of the present invention.

Referring to FIG. 1, a constant amount of waste water per unit time is continuously branched off from the waste water stream 1 (main stream) and is led as so-called measuring stream 2 separately through two measuring cells $M_1$ (also identified as 16) and $M_2$ (also identified as 18), fitted with stirring or mixing devices 10 and 12. In the measuring cell $M_2$, the pH and redox values of the waste water are continuously measured with pH and redox measuring devices. In measuring cell $M_1$ the dosing of acid or alkali takes place, which continuously establishes the pH required for measuring the redox potential. Besides this, the strong oxidizing agent is added to the measuring stream, if the measured redox potential in cell $M_2$ deviates from the desired redox value (set point).

Synchronous with the dosing of the strong oxidizing agent into the measuring stream 2 there is dosed into the waste water stream 1 (main stream) a proportional amount of $H_2O_2$. Additionally, the chemicals needed to regulate the pH in the main stream are added as soon as the strong oxidizing agent is dosed into the measuring stream 2 and $H_2O_2$ is dosed into waste water stream 1 (main stream).

For the exact and quick determination of the $H_2O_2$ requirement which is needed for decreasing the toxic material concentration to the desired limit there must be chosen a strong oxidizing agent which on the one hand reacts practically instantaneously with the toxic materials in the waste water and on the other hand has a comparable oxidation power, to that which is reached by dosing $H_2O_2$ into the waste water stream 1 (main stream) within the available treatment time. As indicated above, under these conditions, the most suitable strong oxidizing agents are the soluble salts of peroxymonosulfuric acid, e.g. sodium monoperoxysulfate and potassium monoperoxysulfate (caroate). However, there can also be used other strong oxidizing agents such as salts of peroxydisulfuric acid, e.g. sodium peroxydisulfate and potassium peroxydisulfate, permanganates, e.g. sodium permanganate and potassium permanganate, ozone and hypochlorites of the alkali metals and alkaline earth metals.

The addition of the $H_2O_2$ as well as the chemicals for pH regulation in the waste water stream 1 (main stream) is undertaken in a mixing vessel $M_H$ (also identified as 20) containing stirring device 22 from which mixing vessel the waste water stream 1 is led into one or more reaction basins 7, 17, 27, and 37 connected in series, in which the oxidation of the various materials present can be carried out simultaneously. In the course of passing these reaction basins, can also, if necessary, a correction of the pH or subsequent dosing of oxidizing agent be carried out.

If insoluble compounds are formed in the oxidative treatment, the waste water stream must subsequently be led to devices for the separation of the sediment (not shown) before the waste water can be led into the sewer. It is also necessary to adjust the pH to the permissible range if it deviates therefrom.

The measuring stream, after passing through the measuring cells $M_1$ and $M_2$, also rejoins the waste water stream 1 (main stream) and the combined treated stream leaves through line 24.

In FIG. 1 the measuring devices are designated by the letters A, B, and C. The lines for dosing of acids, alkali, $H_2O_2$ and caroate into the measuring stream 2 or waste water stream 1 (main stream) are denoted by 3, 4, 5, and 6.

The process of the invention has proved successful above all in the decyanization of blast-furnace gas wash-waters. Such waste waters arise in blast furnace processes in amounts of several hundreds to over one thousand $m^3/h$. They contain besides considerable amounts of flue dust varying amounts of alkali cyanides, heavy metal cyanides, sulfides, sulfites, thiocyanates and other sulfur compounds as well as phenols and other organic compounds. The content of easily-liberated cyanide in these waste waters normally lies in the range of 0–10 mg $CN^-/l$; in disturbances of the blast furnace process or in starting up or shutting down the blast furnace the cyanide content, however, can also increase to a substantially higher value (over 100 mg $CN^-/l$).

For the decyanization of such waste water there has been up to now no suitable process available. The known process of chlorination has disadvantages such as the formation of toxic chlorination products, operation at very high pH values and because of this the formation of additional amounts of neutral salts in the necessary neutralization of the waste water after the detoxification before entering the sewer, which increases the amount of neutral salts arising from the chlorination reagents as well as the known dangers due to the presence of excess chlorine or hypochlorite, entirely apart from the difficulties in automatic monitoring and control of operations with these materials.

In contrast, hydrogen peroxide does not form toxic products or cause additional salting. The presence of an excess is not injurious since hydrogen peroxide decomposes to water and oxygen. The cyanide oxidation with hydrogen peroxide can also be carried out at lower pH values, preferably at pH 10; therefore less chemicals are needed for the alkalization and neutralization of the waste water and therefore less neutral salt is produced. Simultaneously, hydrogen peroxide oxidizes sulfur compounds in a lower stage of oxidation to elemental sulfur or sulfates and thiocyanates are converted into cyanates. In the presence of metallic iron or copper or iron-III ions phenols are also oxidatively broken down by $H_2O_2$ forming mainly dicarboxylic acids. The oxidation of organic compounds takes place partly up to $CO_2$ so that a significant reduction in Chemical Oxygen Demand (COD) is effected by $H_2O_2$ without additional increase in salt content. Aldehydes are also oxidized by $H_2O_2$.

Preliminary experiments have shown that for reduction of the cyanide content in blast-furnace gas wash-water a significantly higher amount of $H_2O_2$ relative to the amount of cyanide is needed because other oxidizable materials sometimes react with the hydrogen peroxide more quickly than cyanide. Such a waste water treatment with $H_2O_2$ can therefore only be carried out if the addition of $H_2O_2$ can be controlled automatically and adjusted according to the total oxidizing agent requirement. This was made possible for the first time through use of the present invention as described in Example 2.

A further field of use for the process of the invention is e.g. the treatment of waste waters from the reproduction section of graphic plants and from film copying works whose content of toxic material in the individual waste water streams as well as in the form of waste water mixtures can be reduced to the desired limit. Besides inorganic sulfur compounds in lower oxidation stages, such waste waters always contain varying amounts of organic compounds which because of their high oxygen demand (COD, BOD) are a great stress for the biological sewage treatment plants. With the help of hydrogen peroxide, it is possible to treat such waste water from fixing, developing and clearing baths and other processes so that the biological load is substantially lower. Thus, by means of the treatment with $H_2O_2$ reducing substances such as thiosulfates and sulfites which are present in fixing, developing, and clearing baths can be finally oxidized up to sulfates. Simultaneously in the oxidation treatment with $H_2O_2$ the dissolved silver is precipitated as an insoluble mixture of $Ag_2O$, $AgBr$ and $Ag_2S$. The recovery of silver from the sludge thus contributes to the cost of the waste water treatment.

In concentrated waste waters from such photo processes the changes in pH or redox potential occurring during the treatment with $H_2O_2$ can frequently be used for control of the oxidative waste water treatment, especially as these treatments can be carried out for the most part batchwise. However, such a waste water treatment is substantially more difficult if a dilute waste water with relatively low concentrations of oxidable materials is used and which, because of the large amounts of waste water, cannot be treated batchwise but must be treated continuously.

In this case the invention is based on the problem of finding a monitoring and regulating concept with whose help it is possible, by dosing $H_2O_2$ into a continuous waste water stream, to lower the iodine value, used here as a measure for the content of oxidizable material, from e.g. above 10 mg iodine/l to 10 mg iodine/l or lower.

To carry out the process of the invention the pH is selected in such a way that the oxidizing agents added to the measuring and waste water main streams can act optimally. This pH value or pH range can be different in the waste water main stream from that in the measuring stream.

Thus, it has been shown that in the oxidation of cyanide-containing waste water the pH in the main stream and in the measuring stream can be in the range of 6 to 12, preferably at about 9-12. The value of about 10 has proved to be especially favorable.

As redox measuring electrodes, platinum, gold, or silver electrodes or an ion sensitive electrode may be used at will and connected with any reference electrodes, e.g. a thalamide electrode.

In employing hydrogen peroxide it may also be of advantage to use activators, e.g. the substances described in German Pat. No. 2,352,856 and Fischer U.S. Pat. No. 3,970,554.

The hydrogen peroxide is employed in the normal commercial concentrations, e.g. in solutions containing 30-70 weight % $H_2O_2$. Higher or lower concentrations are possible, but not usual.

The materials used as strong oxidizing agent such as peroxymonosulfates, peroxydisulfates, potassium permanganate, hypochlorites or ozone are employed in concentrations which are adjusted to the oxidizing agent requirement in each case. In using potassium caroate a concentration of 45 grams $KHSO_5$/l has proven suitable.

Per mole of peroxymonosulfate there are employed 1-10 moles of $H_2O_2$, whereby the ratio of liters of measuring stream to liters of main stream must of course be considered.

For the decyanization of waste waters with $H_2O_2$ in a given case there can also be added a small amount of formaldehyde as an aid, with which the cyanide is partially converted into glycolic acid. The formaldehyde is employed in the form of commercial aqueous solutions which preferably contain 30-40 weight % $H_2CO$. According to the process of the invention additions of 0.1-1 mole of $H_2CO$/mol of peroxymonosulfate are advantageous, in which case again the ratio of liters of measuring stream to liters of main stream must be considered.

The advance in the art of the process of the invention consists essentially of the possibility of ascertaining the requirement of $H_2O_2$ needed for lowering the concentrations of various toxic materials in continuous waste water streams quickly and continuously as well as being able to undertake simultaneously the dosing of the hydrogen peroxide as well as the chemical aids, e.g. for regulation of the required pH in the waste water, so that it is guaranteed that, even at changing concentrations of toxic materials in the waste water, there will always take place the desired breakdown to the required limit of concentration. The process of the invention also has the advantage that the pH regulation in the waste water main stream is only then undertaken if a treatment with hydrogen peroxide is necessary. In this way reagents are saved, as well as unnecessary salting of the waste water.

Unless otherwise indicated all parts and percentages are by weight.

The process of the invention can comprise, consist essentially of, or consist of the stated steps with the stated materials.

The invention is explained more closely in the following examples.

EXAMPLE 1

There should be automatically added to a continuous waste water stream from a film copying plant an amount of $H_2O_2$ corresponding to the varying content of oxidizable materials with substantial avoidance of over and under dosaging. The iodine value serving here as the measure for the content of oxidizable materials should be regulated to a maximum of 10 mg of iodine per liter.

It was established in preliminary tests that the changes of the redox potential at the relatively low concentrations of oxidizable materials (iodine value 100-200 mg per liter) present in the untreated waste water by addition of the $H_2O_2$ were only small and could not be utilized for automatic regulation. The pH of 6–7 present in these water samples did not change substantially during the addition of $H_2O_2$.

However, it was established that, even in these waste waters, significant pH-dependent changes of the redox potential (about 300–400 mV) occur if there is added to the waste water in place of $H_2O_2$, the solution for example of an alkali metal salt of peroxymonosulfuric acid (Caro's acid) such as potassium caroate, $KHSO_5$ (or sodium caroate). This change of the redox potential in the addition of caroate can be used as quantitative control for the treatment of waste water with $H_2O_2$ if the caroate addition is carried out at constant pH and the pH change caused by the addition of the acid-reacting caroate solution is compensated for by addition of caustic soda (aqueous sodium hydroxide). A platinum/calomel-electrode pair is suitable in this case for the potential measurement.

For the principle of the process of the invention see FIG. 1.

For the present example there were branched off from the waste water stream of a film copying plant (about 40 cubic meters per hour) a measuring stream (50 liters per hour) and a main stream with 2300 liters per hour. The measuring stream was led through two series-connected stirrer cells ($M_1$ and $M_2$). There was dosed into the stirrer cell $M_1$ the caroate solution (150 grams of caroate per liter = 6.32 grams of active oxygen per liter) and in the stirrer cell $M_2$ there was dosed 1 N aqueous sodium hydroxide (40 grams of NaOH per liter). The stirrer cell $M_2$ also contains a combined pH-measuring electrode (one-line) and a platinum/calomel redox electrode pair.

With the help of a measuring and controlling apparatus the dosing of the aqueous sodium hydroxide and caroate solution into the measuring stream was controlled in such a manner that, at a constant pH of 8, there was maintained a redox potential of +150 mV. (Under these conditions with potassium iodide-starch paper there was always established a small caroate excess in the measuring stream).

Synchronous with the dosing of caroate into the measuring stream there was added to the main stream a proportional amount of $H_2O_2$ (50 weight % with 281 grams of active oxygen per liter). The waste water treated with $H_2O_2$ flowed through the reactor $M_H$ which consisted of two series-connected reactors, each having a volume of about 750 liters of which the first reactor was equipped with a stirrer. The theoretical residence time amounted to about 20 minutes per reactor.

By determination of the iodine value of the waste water in the main stream treated with $H_2O_2$, the $H_2O_2$ dosage was adjusted so that the iodine value, which in the untreated waste water on the average amounted to 200 mg $I_2$ per liter, was reduced to 10 mg of iodine per liter.

The consumption of chemicals needed to reach this iodine value amounted on the average to:
(a) 400 ml of 1 N-NaOH per hour and 680 ml of caroate solution (150 grams per liter) per hour for the measuring stream (50 liters per hour) and
(b) 940 ml of $H_2O_2$, 50 weight %, per hour for the main stream (2.3 cubic meter per hour).

EXAMPLE 2

At the blast furnace of a metallurgical plant for the production of pig iron there arise per hour about 1,400–1,800 cubic meters of blast-furnace gas wash-water which contains, besides iron oxide and zinc oxide ore and slag particles, calcium compounds etc, varying amounts of dissolved oxidizable materials such as sulfites, sulfides, phenols and also alkali cyanides in the order of magnitude of 0–10 mg $CN^-$ per liter. For example, the total analysis of such a waste water showed the following contents:

2.15 mg $CN^-$/l total cyanide according to DIN 38 405-D 13.1
1.95 mg $CN^-$/l direct argentometrically determinable cyanide
16 ml sediments per liter waste water
0.5 mg Cu/l total
0.3 mg Ni/l total
17 mg Zn/l total
168 mg Fe/l total
0.3 mg Cu/l dissolved in the filtrate
0.2 mg Ni/l dissolved in the filtrate
<0.05 mg Zn/l dissolved in the filtrate
<0.3 mg Fe/l dissolved in the filtrate The pH of the waste was about 6. The permanganate consumption was 1049 mg $KMnO_4$ per liter of waste water corresponding to 265.6 mg active oxygen per liter or 1,130 mg $H_2O_2$ (50 weight percent) per liter or 5,600 mg potassium caroate (45 percent $KHSO_5$) per liter of waste water.

During the temporary shutting-down of the blast furnace for the purpose of repair there was established in the blast-furnace gas wash-water the following maximum content of unwanted substances:
197 mg $CN^-$/l direct argentometrically determinable cyanide
142 mg $CN^-$/l easily-liberated cyanide according to DIN 38 405-D 13.2
820 mg Fe/l total
7.6 mg Pb/l
87.2 mg Zn/l
39 mg $S^{--}$/l DIN stands for German Industrial Standard.

Up to now, the waste water of this blast furnace was merely continuously clarified in a sedimentation plant (Bischoff-basin) and, mixed with other process waters, led into a river; only during the starting-up and shutting-down of the blast furnace, i.e. at higher cyanide contents in the blast-furnace gas wash-water, there was carried out a treatment with hypochlorite bleach solution. This process, however, was not satisfactory because of the above-mentioned side effects.

In the course of investigating all possible processes for the decyanization of this waste water there could also be tested the treatment with hydrogen peroxide using the measuring and control techniques of the invention. Thereby it was found that the content of easily liberated cyanide, (using the residence time in the sedimentation basin, can be quickly and safely reduced to values below 0.1 mg $CN^-$ per liter (according to DIN 38405-D. 13.2) if the ascertained amount of $H_2O_2$ in the waste water determined by redox controlled addition of potassium caroate in a side-stream (measuring stream) is added to the collecting tank installed before the sedimentation plant and simultaneously there is added a less than stoichiometric amount of formaldehyde relative to the amount of $H_2O_2$. In this way, above all at low cyanide concentrations, there is caused a partial conversion into glyconitrile which, under the action of $H_2O_2$, very quickly hydrolyzes to glycolic acid and in the presence of calcium ions substantially precipitates as insoluble calcium glycolate.

Figure 2:
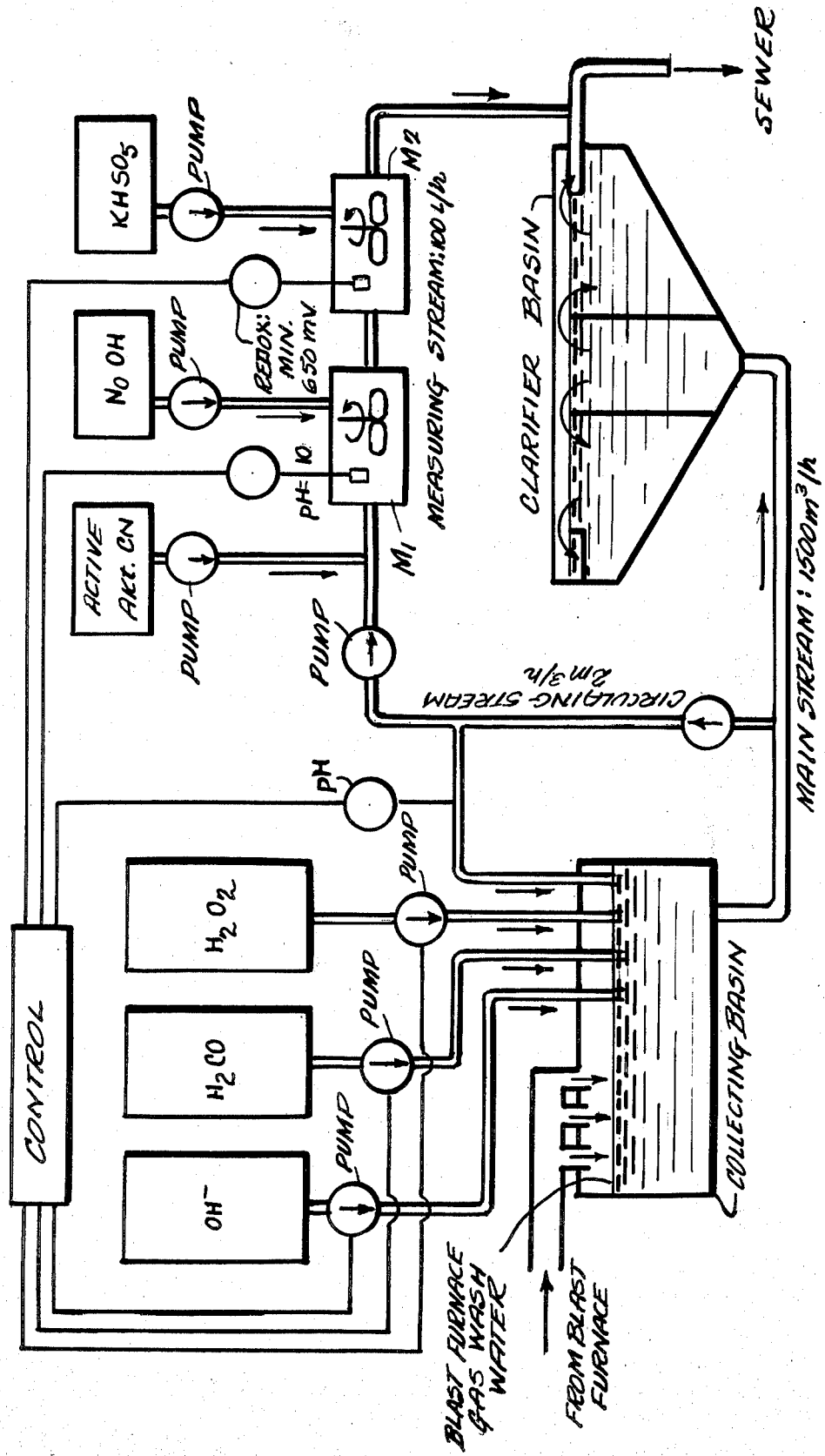
FIG. 2 is a schematic flow diagram of the decyanization of blast-furnace gas wash-water by the process of the invention.

The principle of the measuring and control technique which is employed for the decyanization of the blast-furnace gas wash-water with $H_2O_2$ and $H_2CO$ is represented in FIG. 2.

For the control of the addition of chemicals there is branched off from the blast-furnace gas wash-water stream a side-stream of about 2 cubic meters of waste water per hour and led back again as a loop stream into the collecting tank. From this loop stream there is continuously drawn off exactly 100 liters of waste water per hour and led as a measuring stream through two mixing cells $M_1$ and $M_2$. In the mixing cell $M_1$ the pH of the waste water is continuously measured with a glass electrode and regulated by automatically dosing 10% aqueous sodium hydroxide to pH $10 \pm 0.5$. In the mixing cell $M_2$ the redox potential of the waste water is continuously measured with a silver and a thalamide reference electrode and regulated by automatically dosing a 10% caroate solution containing 4.5% $KHSO_5$ to at least +650 mV. This potential corresponds to the desired degree of detoxification. In order to be able to measure this potential there is continuously dosed into the measuring stream 2 at least 0.001 mg $AgNO_3$ and 2.5 mg KI per liter. The output of the metering pump for the caroate solution was regulated so that in normal operation of the blast furnace the toxic material content could be reduced from maximally 10 mg $CN^-$ per liter in the presence of other oxidizable materials practically instantaneously to a residual content of <0.1 mg $CN^-$ per liter through the added amount of caroate solution, (e.g. dosing output 1 liter of 10% caroate solution per hour). The pump for dosing of caroate solution into the measuring stream is controlled via the set point of the redox measuring device. When the potential falls below the set point (=specified mV value) the pump is switched on, on exceeding the same set point it is switched off again.

Parallel to the dosing of the caroate solution if the potential falls below the set point of the redox measuring amplifier the addition of chemicals into the main stream is also controlled. The pH of the waste water main stream, which already is partly alkalized by lime, is regulated by dosing aqueous sodium hydroxide into the collecting tank to pH $10 \pm 0.5$ with the aid of a pH measuring device in the loop stream line, and proportional amounts of 37% formaldehyde solution and 50 weight percent hydrogen peroxide are also dosed to the collecting tank. The dosing output of the chemical pumps was thereby chosen, so that in the normal operation of the blast furnace and a waste water amount of 1,500 cubic meters per hour there could be dosed per liter of caroate solution (in the measuring stream) 620 liters of $H_2O_2$ (50 weight percent) and 170 liters of $H_2CO$ (37 weight percent) as well as about 3000 liters of NaOH (20 weight percent) in the main stream.

The effective consumption of chemicals in the normal operation of the blast furnace is about 250 liters of $H_2O_2$ (50 weight percent) per hour and 70 liters of $H_2CO$ (37 weight percent) per hour; additionally there is needed on the average 840 liters of NaOH (20 weight percent) per hour for the final alkalization. A re-neutralization of the waste water after the oxidative treatment was not necessary; the pH of the treated waste water after the separation of sediment is always below 9.

An analytical investigation of the degree of detoxification according to DIN 38 405-D 13.2 carried out at regular intervals showed that under these conditions the content of easily-liberated cyanide in the waste water could always be reduced to a value below 0.1 mg $CN^-/l$. The treatment thus fully met the requirements.

If the content of oxidizable material in the waste water increases, both the output of the caroate pump and proportionally that of the chemical pumps for the main stream must be increased. The signal for this is given when, during permanent operation of the chemical dosing pumps, the specified redox potential is no longer exceeded.

In the treatment of blast-furnace gas wash-water it is also necessary to ensure the correct functioning of the measuring electrode by cleaning at regular intervals (about 1 hour), since some materials in the waste water (above all the alkaline earth metal compounds and the $CO_2$) lead in the alkaline pH range to scale formation. Such a cleaning of the electrodes can be effected very easily by dosing into the mixing cell $M_1$ of the measuring stream at regular intervals a small amount of medium strength hydrochloric acid or nitric acid. This dosing is controlled automatically by a time switch.

The entire disclosure of German priority application P 3125452.7 is hereby incorporated by reference.

EXAMPLE 3

In the synthesis of an intermediate for the production of herbicides there arise 1000 l/h of waste water which, in addition to neutral salts and sulfur compounds, also contain other organic reaction products. As a result there is a high COD value of about 17,000 mg $O_2/l$. The pH of the waste water is 7.

Difficulties occurred in treating this waste water in a biological purification plant because of the high COD value. The lowering of the COD value by a complete oxidative treatment with chemicals was excluded for reasons of cost. Therefore the possibility was investigated of changing the materials contained in the waste water by a chemical treatment in such a way that they could be completely broken down in a subsequent biological purification plant.

It was established in preliminary tests that in the treatment of the waste water with $H_2O_2$ in the acid pH range there occurred an intermediate precipitation of certain substances, which in the further oxidation either partially or completely redissolved. However, if the reaction was carried out with less than stoichiometric amount of $H_2O_2$ based on the initial COD of the waste water and the intermediately formed precipitate was separated off, then a substantially greater reduction of the COD was produced than would be expected from the oxidation agents alone. However, this oxidation reaction could not be followed and controlled up to now. Therefore the practical use of these oxidation reactions was linked to high analytical expense. By using the principle of the invention described herein for controlling waste water treatment processes with $H_2O_2$, in this case also a simple and economical solution of the waste water problem was found.

To ascertain the maximum amount of oxidizing agent required, there was continuously branched off from the waste water stream of 1,000 l/h a side-stream of 1 l/h and fed into a diluting water stream of 100 l/h. This diluted waste water side stream was then adjusted to a pH of 12 by dosing aqueous sodium hydroxide solution and there was continuously dosed a caroate solution (45 grams $KHSO_5$/l) until the redox potential measured with a Pt-thalamide electrode pair increased from +700 mV to +800 mV.

Parallel to the diluted waste water side stream, the waste water main stream (1000 l/h) was first adjusted to a pH of 3 by dosing sulfuric acid, and then 50% $H_2O_2$ was always dosed when caroate solution was dosed into the diluted waste water side stream. The ratio of caroate dosed into the diluted waste water to $H_2O_2$ dosed into the waste water main stream was hereby so regulated that in dosing 1 liter of caroate solution into the diluted waste water side stream, there were introduced 16 liters of 50 weight % $H_2O_2$ into the main waste water stream. This amount of $H_2O_2$ corresponds to about 55% of the oxidizing agent requirement for the total oxidation based on the initial COD of the waste water of 17,000 mg $O_2$/l.

After a reaction time of 1.5 hours and separation of the precipitates formed in the course of this treatment, the filtrate of the waste water main stream had a COD value of only 3,570 mg $O_2$/l; this corresponds to a reduction in COD of 79% based on the original COD, or 144% based on the amount of oxidizing agent used.

It was also determined, that the waste water after this treatment could be completely treated in a biological sewage plant without difficulty.

EXAMPLE 4

A continuous waste water stream from a hardening shop which contains varying amounts of nitrite (15 to 120 mg $NO^-_2$/l) should be treated by automatically controlled addition of $H_2O_2$ so that, on the one hand there is guaranteed a complete oxidation of the nitrite to nitrate, and on the other hand that $H_2O_2$ is not dosed in excess.

In preliminary tests on a laboratory scale it was established that in the oxidation of this waste water with $H_2O_2$ in the acid pH range there occurred only a very small change of the redox potential measured with a gold-thalamide electrode pair. This small change could not be used for control.

However, it was also established that in the oxidative treatment of this hardening-shop waste water there always occurred a clear jump in potential (from 320 to 640 mV) if, instead of $H_2O_2$, sodium hypochlorite was used as the oxidizing agent. This change of redox potential can be used as a standard for the treatment of waste water with $H_2O_2$ if the NaOCl addition takes place at a pH below 3 and the change in pH caused by the addition of alkaline NaOCl solution is compensated for by the addition of acid. For the measurement of the potential gold or platinum electrodes are suitable in conjunction with the customary reference electrodes employed in the practice.

CARRYING OUT OF THE OXIDATIVE TREATMENT

There was branched off from the waste water stream of a hardening shop (6 m³/h) for the present example a measuring stream of 100 liters per hour which was led through two measuring cells connected in series. There were fed into the stirrer cell 1 sulfuric acid (accumulator acid) and sodium hypochlorite solution (25 grams NaOCl/l). The stirrer cell 2 contained a combined pH measuring electrode and a gold/thalamide electrode pair.

By using a suitable measuring and control apparatus of customary construction the dosing of acid and NaOCl into the measuring stream was controlled so that at a pH of 3 or below there was maintained a redox potential of above +1600 mV. (Under these conditions with potassium iodide-starch paper there was always established only a slight excess of NaOCl in the measuring stream.)

Parallel to the dosing of NaOCl into the measuring stream, the pH in the main stream was first regulated to 3.5 or below and then there was always dosed a proportional amount of $H_2O_2$, 50 weight %, when NaOCl was dosed into the measuring stream. The thus treated waste water was then led into a further reaction basin (1.5 m³) and from there into final stirrer container (1.5 m³) in which the neutralization with milk of lime was carried out. Then the sediment ($CaSO_4$) contained in the waste water (mainstream and measuring stream) was separated off by means of an inclined clarifier and substantially dewatered in a filter press. In this manner there was always observed in the discharges from the starting clarifier and the filter press a nitrite content below 1 mg $NO^-_2$/l; the excess content of $H_2O_2$ was likewise only less than 5 mg $H_2O_2$/l.

In order to obtain these discharge values there were only needed on the average the following amounts of oxidizing agents (a) 420 ml of hypochlorite solution per hour containing 25 grams NaOCl/l for the measuring stream (100 l/hour).

(b) 520 ml $H_2O_2$, 50 weight %, per hour for the mainstream (6 cbm/hour).

What is claimed is:

1. A process for the treatment of a continuous main waste water stream having a varying content of different oxidizable materials with hydrogen peroxide for the purpose of detoxification and reduction of the chemical oxygen demand and biological oxygen demand, comprising diverting a small portion of the main waste water stream to form a side stream and controlling the amount of hydrogen peroxide added to the main stream by ascertaining the oxidizing agent demand in the side stream by:
    (a) adjusting the pH of the waste water by dosing of alkali or acid continuously to a constant pH value between 3 and 12,
    (b) continuously measuring the redox potential with a platinum, silver, gold, or ion selective electrode and a reference electrode and dosing an aqueous solution of a strong oxidizing agent acting more quickly than $H_2O_2$ under comparable conditions until the desired redox value is reached corresponding to the sought breakdown of the toxic material, and then always when the strong oxidizing agent is dosed into the side stream simultaneously adding into the main stream proportional amounts of $H_2O_2$ and any necessary further chemicals.

2. A process according to claim 1 wherein the materials to be removed are selected from the group consisting of cyanides, sulfides, sulfites, thiosulfates, thiocyanates, and/or organic oxidizable material.

3. A process according to claim 2 wherein the material to be removed includes cyanide.

4. A process according to claim 3 wherein there is added to the main stream a chemical reagent which regulates the pH.

5. A process according to claim 3 wherein the strong oxidizing agent is a peroxymonosulfate, peroxydisulfate, permanganate, hypochlorite or ozone.

6. A process according to claim 5 wherein the strong oxidizing agent is a salt of peroxymonosulfuric acid.

7. A process according to claim 6 wherein the salt is potassium caroate.

8. A process according to claim 6 comprising lowering the cyanide content in the waste water by
   (a) continuously controlling the pH of the side stream to 10±0.5 by adding alkali or acid thereto;
   (b) continuously following the cyanide content in the side stream by measuring the cyanide-specific redox potential with a silver-thalamide electrode pair and dosing an aqueous solution of peroxymonosulfate until there is indicated a redox potential of at least +650 mV; and
   (c) adding to the main stream an amount of hydrogen peroxide potential to the amount of peroxymonosulfate used in the side stream and controlling the pH during the addition to a value between 9 and 12.

9. A process according to claim 8 wherein the pH is controlled in the main stream to 10±0.5.

10. A process according to claim 9 wherein per mole of peroxymonosulfate used in the side stream there is fed into the main stream 1–10 moles of $H_2O_2$ times the ratio of liters in the main stream to the liters in the side stream.

11. A process according to claim 10 wherein there is fed into the main stream 0.1–1 mole of formaldehyde per 1–10 moles of $H_2O_2$.

12. A process according to claim 8 wherein per mole of peroxymonosulfate used in the side stream there is fed into the main stream 1–10 moles of $H_2O_2$ times the ratio of liters in the main stream to the liters in the side stream.

13. A process according to claim 12 wherein there is fed into the main stream 0.1–1 mole of formaldehyde per 1–10 moles of $H_2O_2$.

14. A process according to claim 2 wherein there is added to the main stream a chemical reagent which regulates the pH.

15. A process according to claim 2 wherein the strong oxidizing agent is a peroxymonosulfate, peroxydisulfate, permanganate, hypochlorite or ozone.

16. A process according to claim 15 wherein the strong oxidizing agent is a salt of peroxymonosulfuric acid.

17. A process according to claim 16 wherein the salt is potassium caroate.

18. A process according to claim 15 wherein there is employed as the strong oxidizing agent a peroxymonosulfate and per mole of peroxymonosulfate used in the side stream there is fed into the main stream 1–10 moles of $H_2O_2$ times the ratio of liters in the main stream to the liters in the side stream.

19. A process according to claim 15 wherein the waste water contains a sulfur compound which is a sulfide, sulfite, or thiosulfate and the content of the sulfur compound can be expressed by the iodine value which is the iodine consumption of the waste water in mg I/l and the process comprising reducing the iodine value by
   (a) continuously controlling the pH of the side stream to a constant pH in the range of 3 to 12 by adding acid or alkali;
   (b) continuously feeding into the side stream an aqueous solution of peroxymonosulfate whose amount is regulated so that therewith the redox potential of the side stream is continuously maintained at a constant mV value which is characteristic for a specific predetermined reduction of the iodine value;
   (c) adding to the main stream an amount of hydrogen peroxide proportional to the consumption of peroxymonosulfate in the side stream and controlling the pH to a value between 3 and 12.

20. A process according to claim 19 wherein the pH in the side stream is controlled to a value between 6 and 10 and the pH in the main stream is controlled to a value between 6 and 10.

* * * * *